United States Patent
Dwivedi et al.

(10) Patent No.: US 6,740,639 B1
(45) Date of Patent: May 25, 2004

(54) INCLUSION COMPLEES OF A HIGH POTENT OPIOID PEPTIDE, PHARMACEUTICAL COMPOSITIONS AND METHOD OF TREATMENT

(75) Inventors: Anil Kumar Dwivedi, Lucknow (IN); Madhu Khanna, Lucknow (IN); Wahajul Haq, Lucknow (IN); Ram Raghubir, Lucknow (IN); Sudhir Srivastava, Lucknow (IN); Puvvada Sri Ramchandra Murthy, Luckno (IN); Onkar Prasad Asthana, Lucknow (IN); Jagdishwar Sahay Srivastava, Lucknow (IN); Satyawan Singh, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/537,088

(22) Filed: Mar. 29, 2000

(51) Int. Cl.[7] .............................. A61K 38/08; C07K 7/06
(52) U.S. Cl. ........................ 514/17; 530/302; 530/330
(58) Field of Search ................................ 514/17; 530/302, 530/330

(56) References Cited

U.S. PATENT DOCUMENTS 5,855,916 A * 1/1999 Chiesi et al. ................ 424/488
5,997,856 A * 12/1999 Hora et al. ................. 424/85.2

FOREIGN PATENT DOCUMENTS

EP   463653   * 1/1992
FR  2710268   * 3/1995

OTHER PUBLICATIONS

Nath et al. Novel Met–Enkephalin Analogue1 . . . Pharm. Res. vol. 31, No. 5, pp. 269–273, 1995.*

* cited by examiner

Primary Examiner—Jeffrey E. Russel
(74) Attorney, Agent, or Firm—Nath & Associates PLLC; Harold L. Novick; Joshua B. Goldberg

(57) ABSTRACT

The invention provides novel inclusion complexes of highly potent opioid peptide of L-Tyrosyl-D-alanyl-glycyl-N-methylphenylalanyl-glycyl-isopropylamide with cyclodextrin, pharmaceutical preparations containing these inclusion complexes of L-Tyrosyl-D-alanyl-glycyl-N-methylphenylalanyl-glycyl-isopropylamide with cyclodextrin derivatives, the complexes being better soluble in water and having improved biopharmaceutical properties such as lesser toxicity, better analgesic action and non-addiction properties.

11 Claims, 11 Drawing Sheets

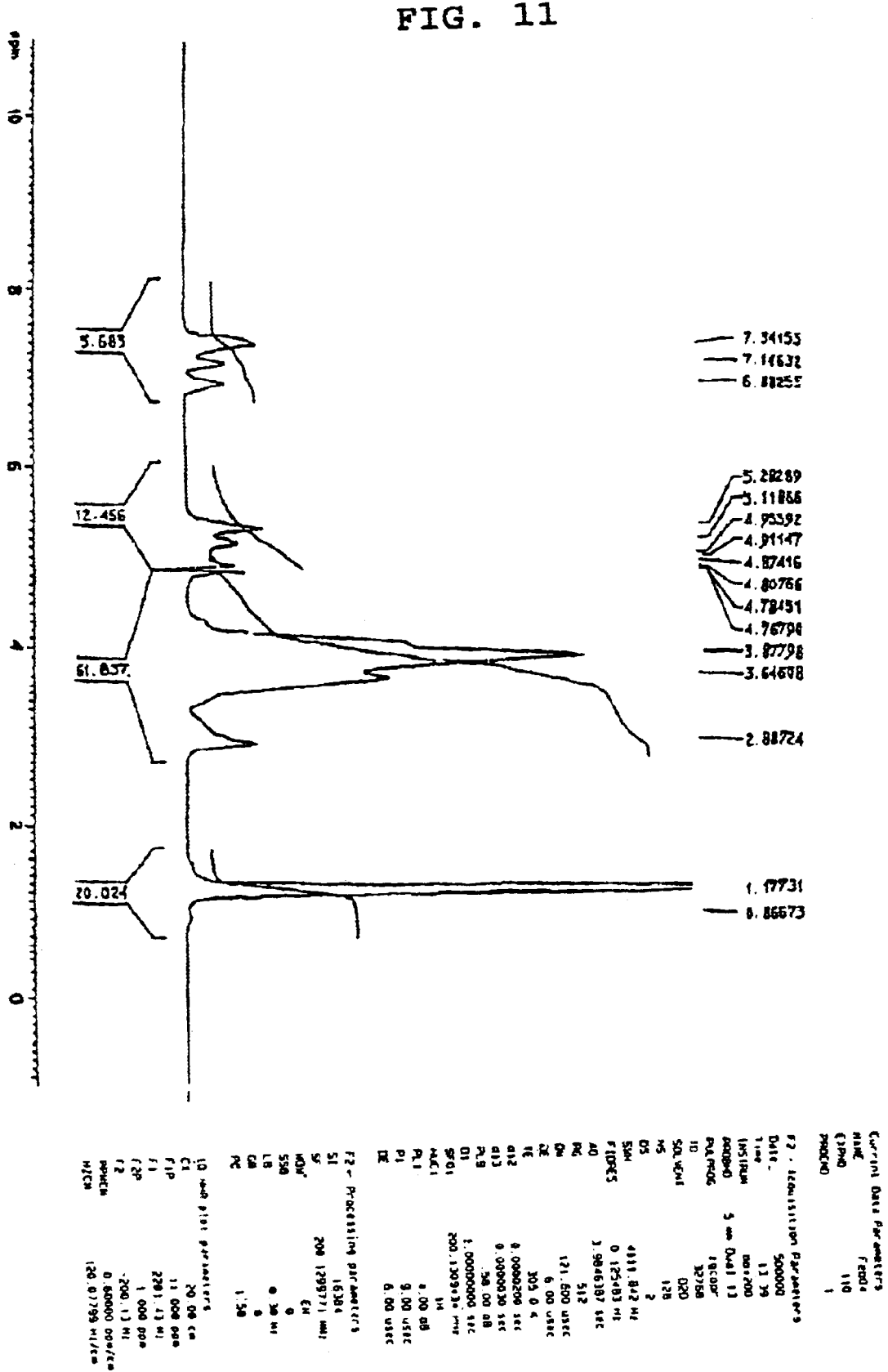

INCLUSION COMPLEES OF A HIGH POTENT OPIOID PEPTIDE, PHARMACEUTICAL COMPOSITIONS AND METHOD OF TREATMENT

FIELD OF THE INVENTION

The present invention relates to novel inclusion complexes of a high potent opioid peptide, Tyrosyl-D-alanyl-glycyl-N-methylphenylalanyl-glycyl-isopropylamide with cyclodextrin derivative. More particularly, the invention relates to Tyrosyl-D-alanyl-glycyl-N-methylphenylalanyl-glycyl-isopropylamide with cyclodextrin derivatives such as beta-cyclodextrin, hydroxypropyl-beta cyclodextrin, hydroxyethyl-beta-cyclodextrin, or Dimethyl-beta cyclodextrin. The invention also relates to a process for the preparation of pharmaceutical compositions containing the inclusion complexes of opiod peptide and the use thereof in the treatment of alleviating pain and acute inflammation, which can be used as a substitute- for narcotic analgesics.

BACKGROUND OF THE INVENTION

There exists a constant need for preparing novel centrally acting agents which can be utilized as substitute for the narcotic analgesics, currently being used, having improved biopharmaceutical properties such as low toxicity, lesser tolerance, longer duration of action and least abuse potential. The development of the peptide as drug is restricted due to its poor oral efficacy. In view of this, it is essential to develop orally active formulations. There has been tremendous emphasis on the development of innovative strategies for the oral delivery of peptide based, drugs, with increased water solubility, dissolution, bioavailability and improved oral efficacy.

PRIOR ART

Soon after the discovery of enkephalin by Huges et. Al [Huges et. Al, Nature 258, 577 (1975)]. an endogenously occurring pentapeptide with morphinomimetic activity, structure activity relationship studies were undertaken world-wide with the objective of getting a synthetic congener that would be clinically acceptable pain killer as substitute to morphine. Since the analgesia evoked by enkephalins was only weak and transient following their administration by intra-cerebral route, greater emphasis was laid on the structural modification of the penta peptide which would lead to the peptide(s) capable of eliciting profound analgesis even after their systemic administration.

The two best enkephalin analogues that had undergone fairly extensively clinical studies so far, are the Sandoz compound FK-33-824 [Tyr-D-Ala-Gly,-Met(o)-01] and the Lilly compound met-keohamid (Tyr-D-Ala-Gly-Phe-MeMet-NH2). [Von Graffenreid, B., del Pozo, E., Roubicek, J., Krebs, E., Poldinger, W., Burmeister, P. and Kerp, L., Nature, 272, 729 (1978) and, Frederickson, R. C. A., Smithwick, E. L., Shuman, R. and Bernis, K. G., Science, 211, 603, (1981) Frederickson, R. C. A., In "Opioid Peptides: Molecular Pharmacology, Bio synthesis and analysis" Rapaka, R. S. and Hawks, R. L. eds. NIDA Research Monograph, 70 367. (1986)] FK-33-824 gave only slight preference for p-receptors and met-kephamid was found essentially non-elective for $\mu$ and $\delta$ receptors. A strong analgesic effect was exerted by both the compounds by systemic route of administration. However, due to a number of serious side effects produced by FK-33-824 therefore it was no longer pursued for further developments as candidate analgesic drug. Relatively fewer side effects were observed with met-kephamid, but due to its hypotensive effect this compound was also finally abandoned.

Another enkephalin analogs Tyr-D-Met-Gly-Phe-Pro-NH$_2$ [Flodes, J., torok, K., Szekeley, J. I., Borvenderg, J., Karezag, I., Tolna, J., Marosfi, S., Varadi, A., Gara. A., Ronai. A. Z. and Szilaggi, G. Life Sciences 33, Supp. 1, 769 (1983)] and Tyr-Arg-Gly-Phe(pNO$_2$)-Pro-NH$_2$ (BW-443C) (SEQ ID NO. 1) [Follenfani, R. I., Hardy, G. W., Lowe, L. A., Schneider, C. and Smith, T. W. Br. J. Pharmacol. 93, 85, (1988) and Kriss, M. G., Gralla, R. J., Clark, R. A., Tyson, L. B. and Groshen, S., J. Clin. Onclol., 6, 663, (1988)] were also shown to be more potent analgesic than morphine but due to number of side effects these compounds were also dropped after initial clinical trials. Similarly, structure activity relationship studies were undertaken in our laboratory and an enkephalin analog Tyr-D-Ala-Gly-MePhe-Gly-NHC$_3$H$_7$ [Raghubir, R., Patnaik, G. K., Sharma, S. D., Mathur, K. B. and Dhawan B. N., In recent progress in chemistry and biology of centrally acting peptides. Dhawan B. N. and Rapaka R. S. eds., .167, (1988) and Indian Patent no. 173568 19.10.1989] synthesized earlier in our laboratory and found to be more potent than morphine following systemic administration. This is a highly $\mu$-receptor selective in central and peripheral assay and produces highly profound and long lasting analgesia. (C. Nath, G. K. Patnaik, W. Haq, K. B. Mathur, R. C. Srimal, B. N. Dhawan and F. Porreca, Pharmacological Research, 31, 269–273, 1995) The compound and its process for the synthesis was first disclosed in Indian patent [Indian Patent no. 173568 19.10.1989]. Subsequently chronic and subacute toxicity studies on this compound were carried out and it is now disclosed that this compound is safe and did not produce any noticeable toxic side effects. This compound was also studied for their addiction liabilities and tolerance and found to elicit significantly reduced tolerance and addiction properties as compared to morphine. The compound is virtually devoid of any major CNS effects like sedation and respiratory depression; it is also virtually devoid of any significant cardiovascular effects. Therefore, this compound has .a potential as centrally active analgesic agent, which can be used as a substitute to narcotic analgesics (Morphine and related substances). However, this compound upon oral administration produced poor response and extremely high dose is required to obtain similar magnitude of response as observed after parenteral administration owing to its decomposition and poor absorption. The oral efficacy of the therapeutic agents is considered to be highly desirable, therefore, inspite of a profound analgesia and favourable pharmacological effect and almost devoid of toxic effects, the. development of the peptide as drug is restricted due to its poor oral efficacy. In view of this, it is essential to develop orally active formulations.

There has been. tremendous emphasis on the development of innovative strategies for the oral delivery of peptide based drugs, (A Fasano. (1998) TIBTECH., 16, 152–157) with increased water solubility, dissolution, bioavailability and improved oral efficacy (Z. Shao, 1992). Cyclodextrins are reported in the literature that they increase water solubility, dissolution, bioavailability and stability of compound by forming inclusion complexes. [R. Krishnamoorthy and A. K. Mitra, Pharma. Res., 9: 1157–1163 (1992)]. Recently it was reported in the literature that the β-cyclodextrin inclusion complex increase the half life of Leu-enkephalin from 45 min to 75 min in case of enzyme hydrolysis with leucine amino peptidase (W. J. Erwin., A. K. Dwivedi, P. A. Holbrook, and M. J. Dey, Pharma Res., 11, 1994, 1698–1703). Therefore, the preparation of inclusion complex of peptides and other substances with cyclodextrin are reported in the literature. The advantage of binding substances into inclusion complexes with cyclodextrin is also known in other substances. U.S. Pat. Nos. 4,603,123, 5,840, 714 and 5,855,916 disclosed the increased therapeutic efficacy and reduced toxic effects of piroxicam, ibuproxam and acid base type drugs respectively.

OBJECTS OF THE INVENTION

The main object of the present invention is to provide novel L-Tyrosyl-D-alanyl-glycyl-N-methylphenylalanyl-glycyl-isopropylamide: cyclodextrin complexes having significantly improved oral efficacy and prolonged duration of acion.

Another object is to provide novel inclusion complexes that can be utilised as substitute for narcotic analgesics, said complexes having improved biopharmaceutical properties such as low toxicity, lesser tolerance, longer duration of action and least abuse potential.

Still another object is to provide novel L-Tyrosyl-D-alanyl-glycyl-N-iniethylphenylalanyl-glycyl-isopropylamide complexes with increased water solubility, dissolution, bioavailability and improved oral/transdermal efficacy.

Yet another object is to provide pharmaceutical compositions containing said novel inclusion complexes having improved analgesic activity with longer duration of activity and improved efficacy.

Still another object is to provide methods for the treatment of acute inflamnmatory conditions employing the said inclusion complexes.

SUMMARY OF THE INVENTION

The above and other objects are realized by the present invention that provides novel inclusion complexes having improved analgesic prope and longer duration of activity. The invention also provides pharmaceutical compositions containing said inclusion complexes and methods of treatment employing such inclusion complexes.

BRIEF DESCRIPTION OF THE DRAWINGS

FIG. 11 shows NMR spectrum of the complex of L-Tyrosyl-D-alanyl-glycyl-N-methylphenylalanyl-glycyl-isopropylamide with hydroxypropyl-beta-cyclodextrin.

DETAILED DESCRIPTION

Figure 1:
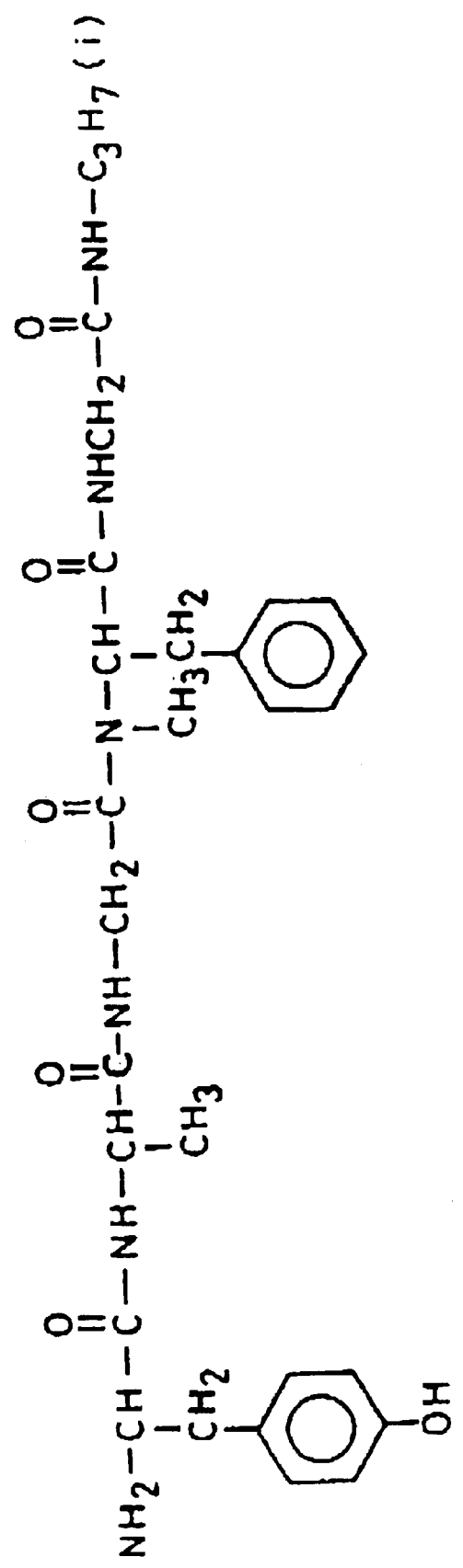
FIG. 1 shows the preparation of L-Tyrosyl-D-al.anyl-glycyl-N-methylphenylalanyl-glycyl-isopropylamide.

Accordingly, the invention provides novel inclusion complexes having significantly improved oral efficacy and prolonged duration of action selected from the group consisting of highly potent opioid peptide of L-Tyrosyl-D-alanyl-glycyl-N-methylphenylalanyl-glycyl-isopropylamide with a cyclodextrin derivative wherein said derivative is selected from the group consisting of beta cyclodextrin, hydroxypropyl-beta cyclodextrin, dimethyl-beta cyclodextrin and hydroxyethyl-beta-cyclodextrin.

In an embodiment, the invention provides cyclodextrin derivative selected from beta cyclodextrin, hydroxypropyl-beta cyclodextrin, dimethyl-beta cyclodextrin, hydroxyethyl-beta-cyclodextrin.

In yet another embodiment, the inclusion complex comprises L-Tyrosyl-D-alanlyl-glycyl-N-methylphenylalanyl-glycyl-isopropylamide with beta,-cyclodextrin.

In still another embodiment, the inclusion complex comprises L-Tyrosyl-D-alanyl-glycyl-N-methylphenylalanyl-glycyl-isopropylamide with beta-cyclodextrin.

In another embodiment, the inclusion complex comprises L-Tyrosyl-D-alanyl-glycyl-N-methylphenylalanyl-glycyl-isopropylamide with dimethyl beta,-cyclodextrin.

In still another embodiment, the molar ratio between L-Tyrosyl-D-alanyl-glycyl-N-methylphenylalanyl-glycyl-isopropylamide and said cyclodextrin derivative is 1:5 to 2:1.

In yet another embodiment, the invention provides pharmaceutical compositions comprising a therapeutically effective amount of inclusion complex of L-Tyrosyl-D-alanyl-glycy-N-methylpheylalanyl-glycyl-isopropylamide with beta-cyclodextrin having improved analgesic activity with longer duration of action as compared with the free peptide.

In yet another embodiment the pharmaceutical composition has potential for clinical application as an analgesic.

In still another embodiment, the pharmaceutical composition is formulated in various physical forms such as tablets, injections, capsules.

The invention also provides methods for the treatment of acute inflammations and for alleviating pain comprising the step of administration of pharmaceutical composition containing the inclusion complex to a patient in need thereof In an embodiment, the inclusion complex is administered orally or transdermally or rectal route.

In yet another embodiment, the pharmaceutical composition exhibits significant analgesic activity with reduced dependence liability, respiratory depression, gastric irritation and sedation.

In another embodiment, the method for the treatment of acute inflammations and for alleviating pain, comprises oral administration of inclusion complex of L-Tyrosyl-D-alanyl-glycyl-N-methylphenylalanyl-glycyl-isopropylamide with beta-cyclodextrin.

In another embodiment, the method for the treatment of acute inflammations and for alleviating pain, comprises topical application of inclusion complex of L-Tyrosyl-D-alanyloycyl-N-methylphenylalanyl-glycyl-isopropylamide with beta cyclodextrin.

The L-Tyrosyl-D-alanyl-glycyl-N-methylphenylalanyl-glycyl-isopropylamide: cyclodextrin (1.2) complex of the invention is used for the oral delivery of the peptide as these complexes provide more protection to the peptide against the gastric environment. The L-Tyrosyl-D-alanyl-glycyl-N-methylphenylalanyl-glycyl-isopropylamide: cyclodextrin (1:1) complex is used for the transdermal delivery of the peptide as these complexes facilitate the transdermal permeation of the peptide.

Methods of Preparation

Technical Solution

The invention is illustrated by the following Examples which in no way represent a limitation thereof

EXAMPLE 1

Preparation of L-Tyrosyl-D-alanyl-glycyl-N-methylphenylalanyl-glycyl-isopropylamide [FIG. 1]

The penta-peptide was synthesised by solution phase method of peptide synthesis employing three plus two fragment condensation method or by step up chain elongation procedure. This compound was also prepared on solid support employing commercially available supports using either BOC or FMOC chemistry. The coupling reactions were performed by commonly available reagents adopting reported procedures. The out line of the process for the preparation of the penta-peptide has been disclosed in Indian Patent No. 173568 19.10.1989.

Figure 2:
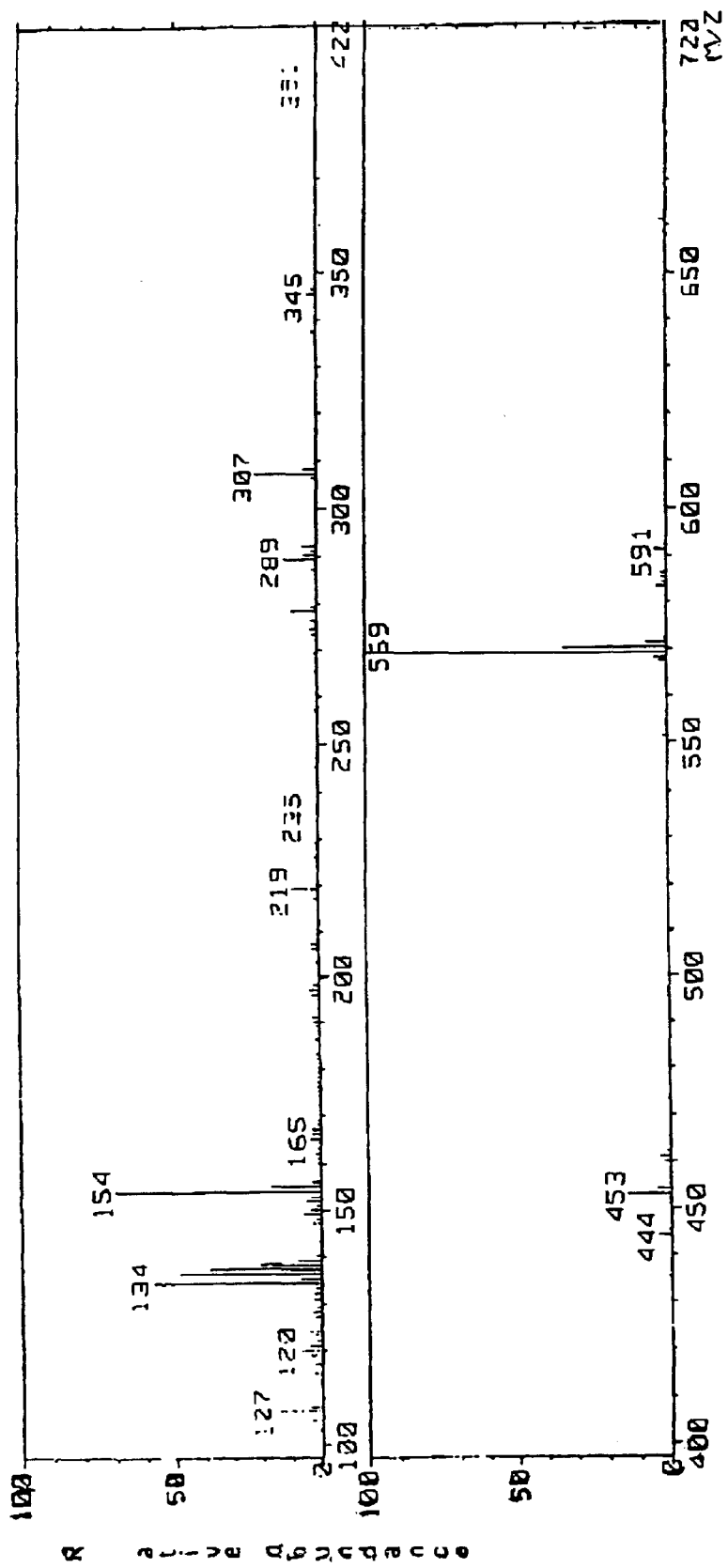
FIG. 2 shows mass spectrum of L-Tyrosyl-D-alanyl-glycyl-N-methylphenylalanyl-glycyl-isopropylamide.

FIG. 2 shows Mass spectrum of L-Tyrosyl-D-alanyl-glycyl-N-methylphenylalanyl-glycyl-isopropylamide.

Figure 3:
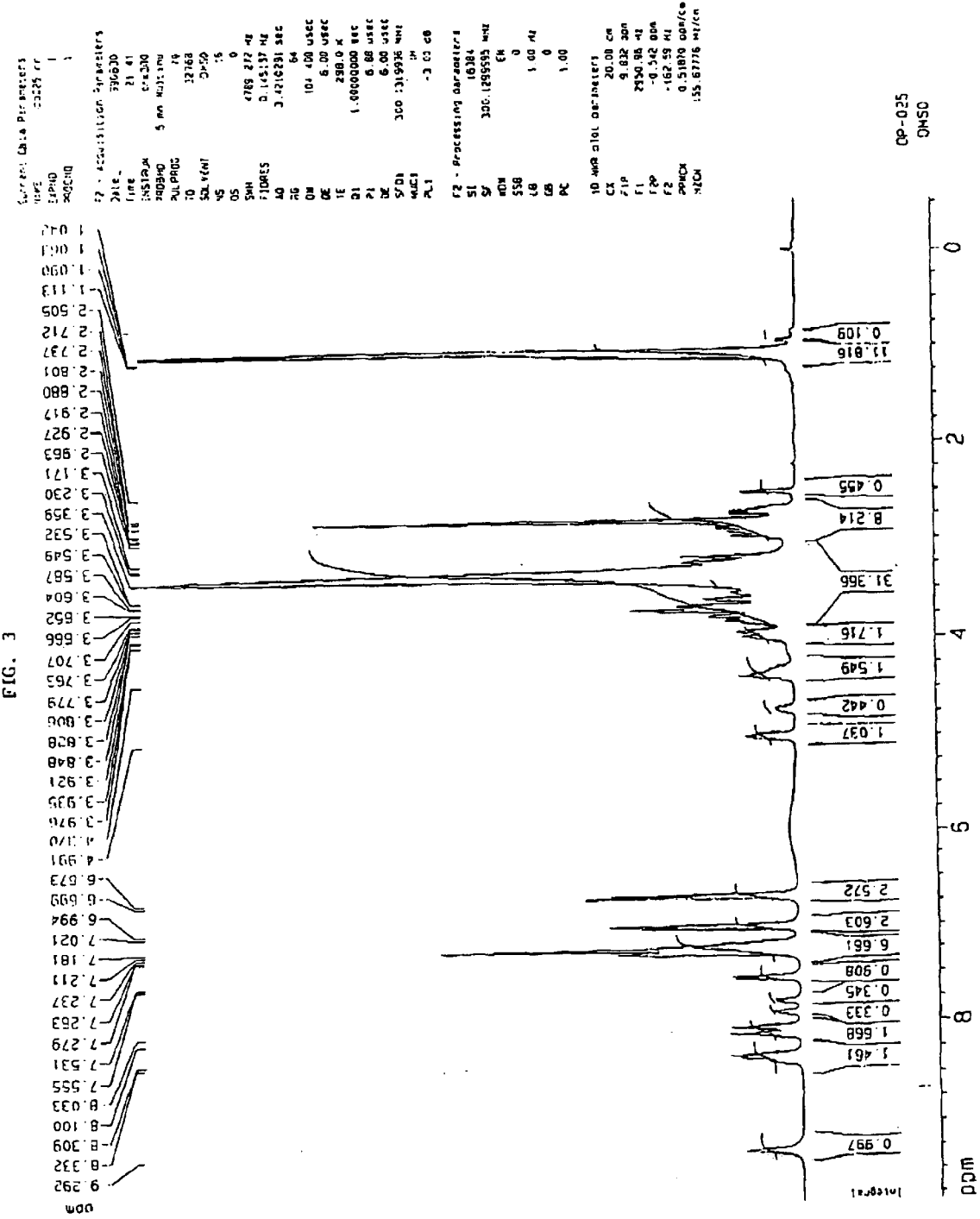
FIG. 3 shows NMK spectrum of L-Tyrosyl-D-alanyl-glycyl-N-methylphenylalanyl-glycyl-isopropylamide.

FIG. 3 show No spectrum of L-Tyrosyl-D-alanyl-glycyl-N-methylphenylalanyl-glycyl-isopropylamide.

Figure 4:
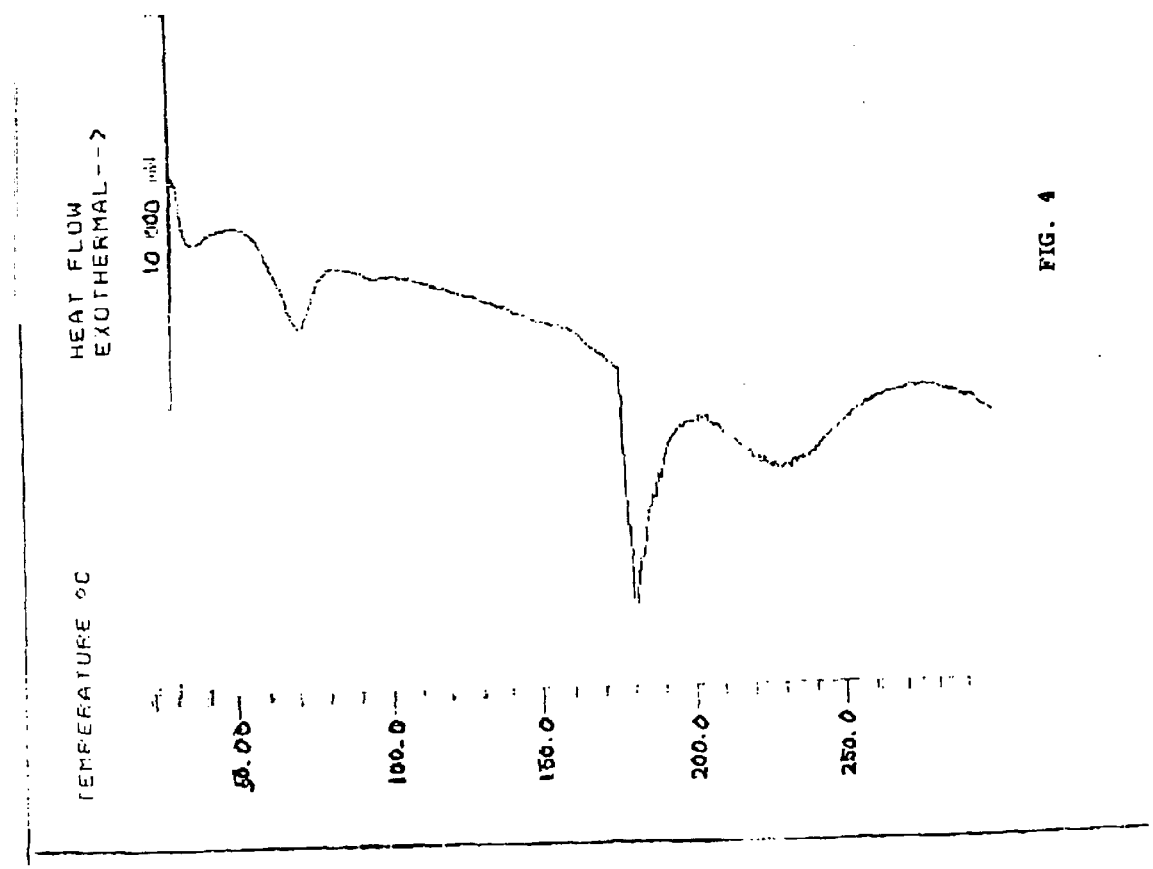
FIG. 4 shows DSC (differential scanning calorimetry) thermogram of L-Tyrosyl-D-alanyl-glycyl-N-methylphenylalanyl-glycyl-isopropylamide.

FIG. 4 shows DSC (differential scanning calorimetry) thermogram of L-Tyrosyl-D-alanyl-glycyl-N-methylphenylalanyl-glycyl-isopropylamide.

EXAMPLE 2

Preparation of inclusion complex of L-Tyrosyl-D-alanyl-glycyl-N-methylphenylalanyl-glycyl-isopropylamide with beta-cyclodextrin a) Procedure in Aqueous Medium Beta-cyclodextrin (1.135 g 1.0 m mole) in water (25 ml) was heated to boiling temperature. L-Tyrosyl-D-alanyl-glycyl-N-methylphenyl-alanyl-glycyl-isopropylamide (0.568 g 1.0 m mole) was added into this solution vigorously stirred for 15 minutes and the mixture was cooled during stirring to a temperature between 0 degree and 5 degree centigrade. The obtained complex was dried in vacuum at the temperature of about 40 degree C. Inclusion complex (1.62 g. 95.1%) of L-Tyrosyl-D-alanyl-glycyl-N-methylphenylalanyl-glycyl-isopropylamide with beta-cyclodextrin was obtained in the farm of a white powder in the molar ratio of 1:1.

Data on reaction yields, L-Tyrosyl-D-alanyl-glycyl-N-methylphenyl-alanyl-glycyl-isopropylamide content in the complex (determined theoretically and experimentally-spectrophotometric determination at the wavelength of 275 nm) are summarised in Table I.

Figure 5:
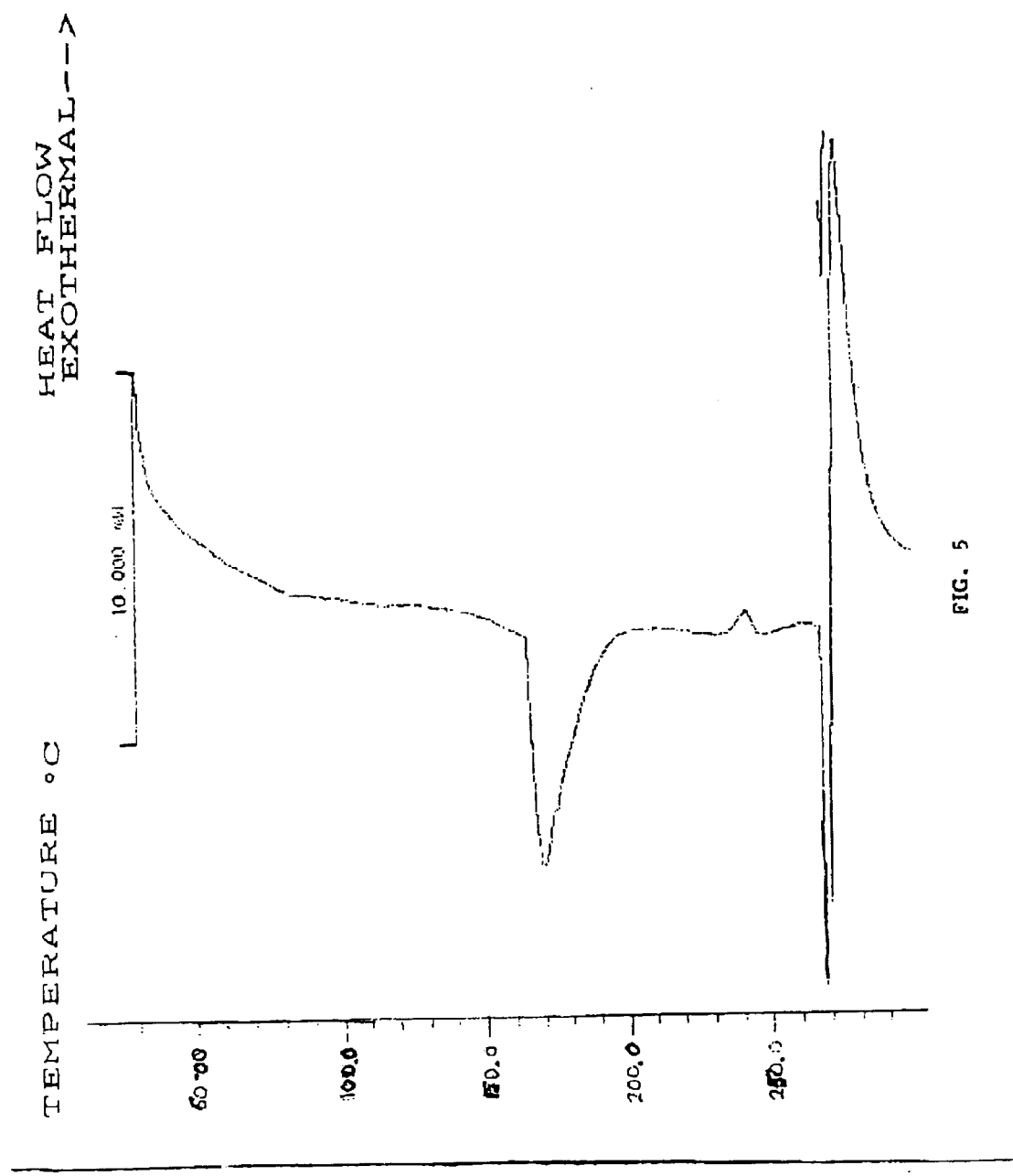
FIG. 5 shows DSC thermogram in the curve of the obtained product.

FIG. 5 shows Differential scanning calorimetry (DSC thermogram) in the curve of the obtained product. There was not detected any endothermic transition for a melting point, characteristic of a physical mixture of L-Tyrosyl-D-alanyl-glycyl-N-methylphenylalanyl-glycyl-isopropylamide.

Figure 6:
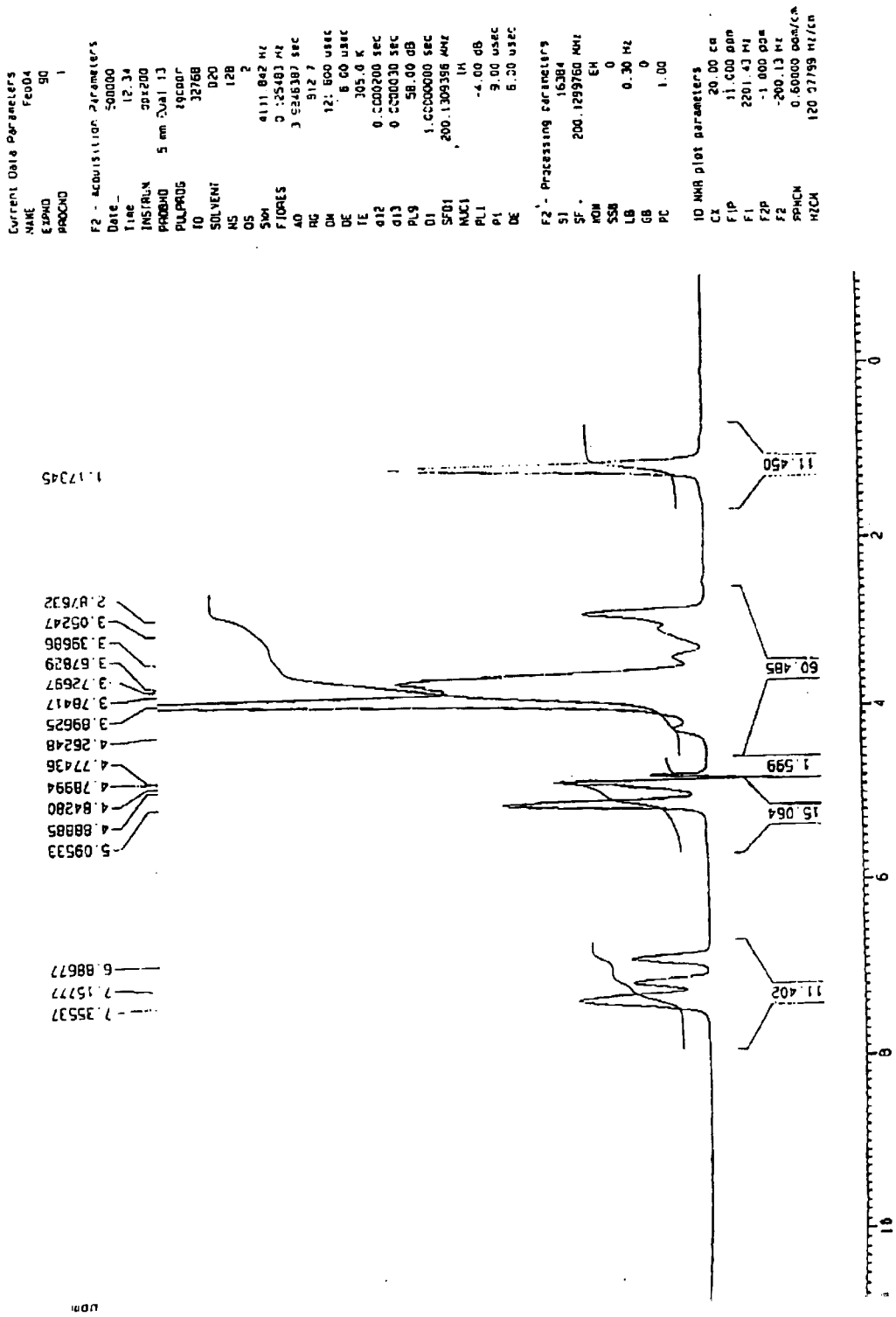
FIG. 6 shows NMR spectrum of the complex of L-Tyrosyl-D-alanyl-glycyl-N-methylphenylalanyl-glycyl-isopropylamide with beta-cyclodextrin.

FIG. 6 shows NMR spectrum of the complex of L-Tyrosyl-D-alanyl-glycyl-N-methylphenylalanyl-glycyl-isopropylamide with beta-cyclodextrin.

Figure 7:
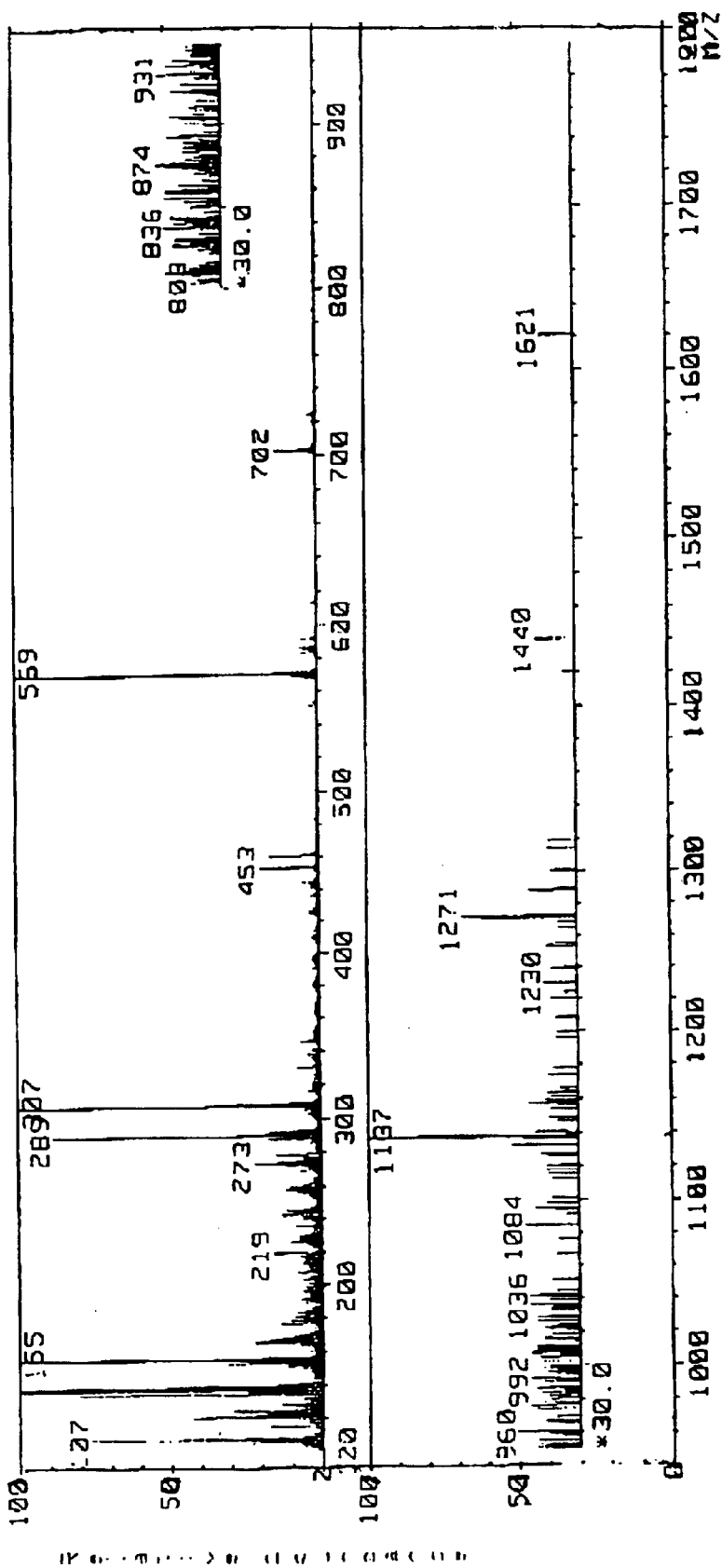
FIG. 7 shows mass spectrum of the complex of L-Tyrosyl-D-alanyl-glycyl-N-methylphenylalanyl-glycyl-isopropylamide with beta-cyclodextrin.

FIG. 7 shows Mass spectrum of the complex of L-Tyrosyl-D-alanyl-glycyl-N-methylphenylalanyl-glycyl-isopropylamide with beta-cyclodextrin.

b) Procedure in a Solvent Mixture (Methanol/Water in the Ratio 5.20)

Beta.-cyclodextrin (1.135 g; 1.0 m mole) was dissolved in water (25 ml) at a temperature of about 70 degree C. During stirring a solution of L-Tyrosyl-D-alanyl-glycyl-N-methylphenylalanyl-glycyl-isopropylamide (0.568 g, 1.0 m mole) in methanol (5 ml) was added. It was stirred for another 5 minutes, the solvents were evaporated and the obtained complex was dried in vacuum at a temperature about 40 degree C. Inclusion complex (1.59 g, 93.4%) of L-Tyrosyl-D-alanyl-glycyl-N-methylphenylalanyl-glycyl-isopropylamide with beta-cyclodextrin was obtained in the form of a white powder in the molar ratio of 1 1. Differential scanning calorimetry, mass and NMR spectrum showed the same results as in the process for preparing the inclusion complex in an aqueous medium.

EXAMPLE 3

Preparation of inclusion complex of L-Tyrosyl-D-alanyl-glycyl-N-methylphenylalanyl-glycyl-isopropylamide with beta-cyclodextrin a) Procedure in Aqueous Medium Beta.-cyclodextrin (1.135 g; 1.0 m mole) in water (25 ml) was heated to boiling temperature, into the boiling solution of L-Tyrosyl-D-alanyl-glycyl-N-methylphenyl-alanyl-glycyl-isopropylamide (0.294 g; 0.5 m mole) was added, vigorously stirred for 15 minutes and the mixture was cooled during stirring to a temperature between 0 degree and 5 degree C. The obtained complex was dried in vacuum at the temperature of about 40 degree C. Inclusion complex (1.33 g; 93.7%) of L-Tyrosyl-D-alanyl-glycyl-N-methylphenyl-alanyl-glycyl-isopropylamide with beta.-cyclodextrin was obtained in the form of a white powder in the molar ratio of 1:2.

Data on reaction yields, L-Tyrosyl-D-alanlyl-glycyl-N-methylphenylalanyl-glycyl-isopropylamide content in the complex (determined theoretically and experimentally-spectrophotometric determination at the wavelength of 275 nm) are summarised in Table 1.

Figure 8:
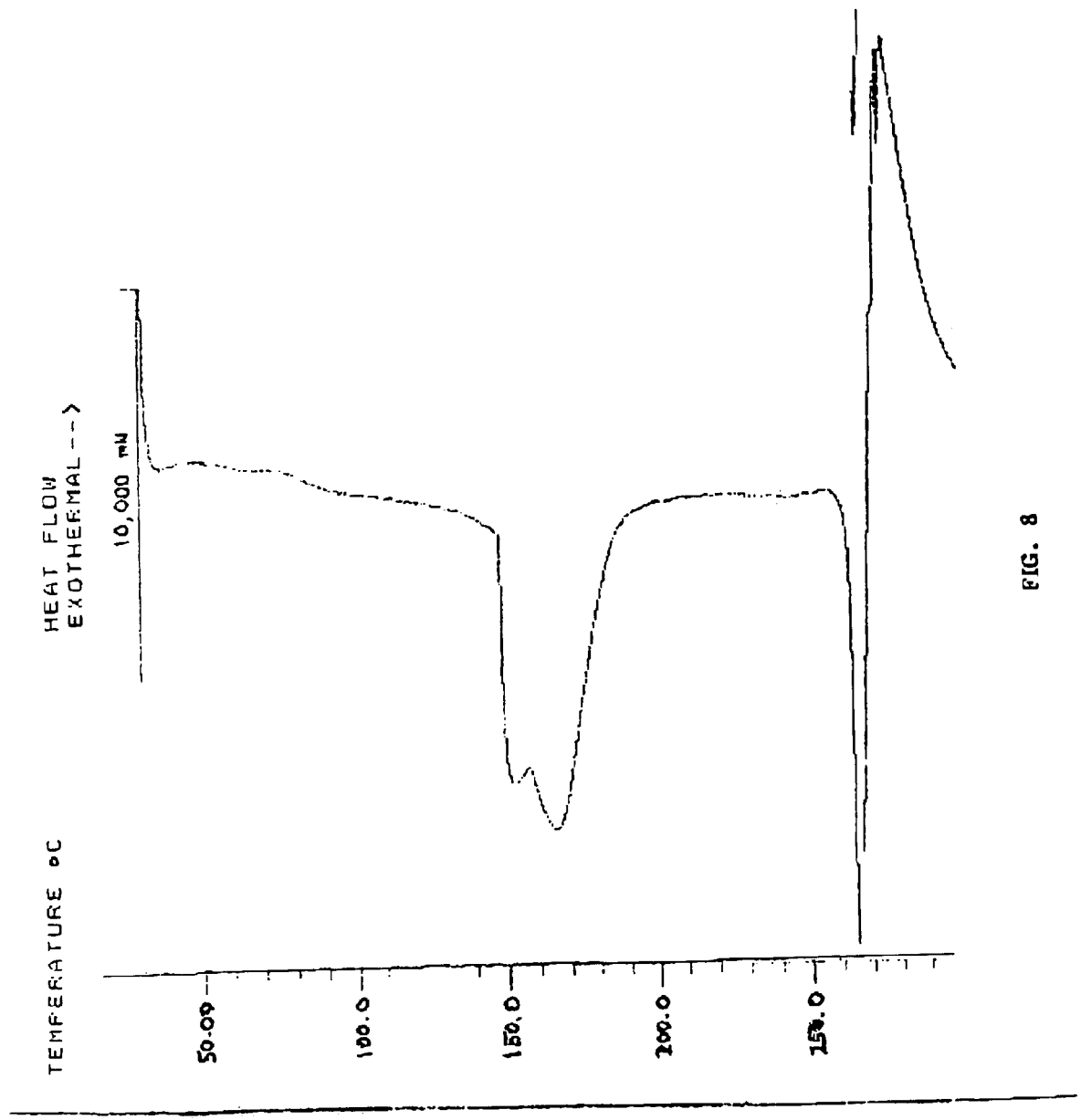
FIG. 8 shows DSC thermogram in the curve of the obtained product.

FIG. 8 shows Differential scanning calorimetry (DSC thermogram) in the curve of the obtained product there was not detected any endothermic transition for a melting point, characteristic of a physical mixture of L-Tyrosyl-D-alanyl-glycyl-N-methylphenylalanyl-glycyl-isopropylamide/beta-cyclodextrin.

Figure 9:
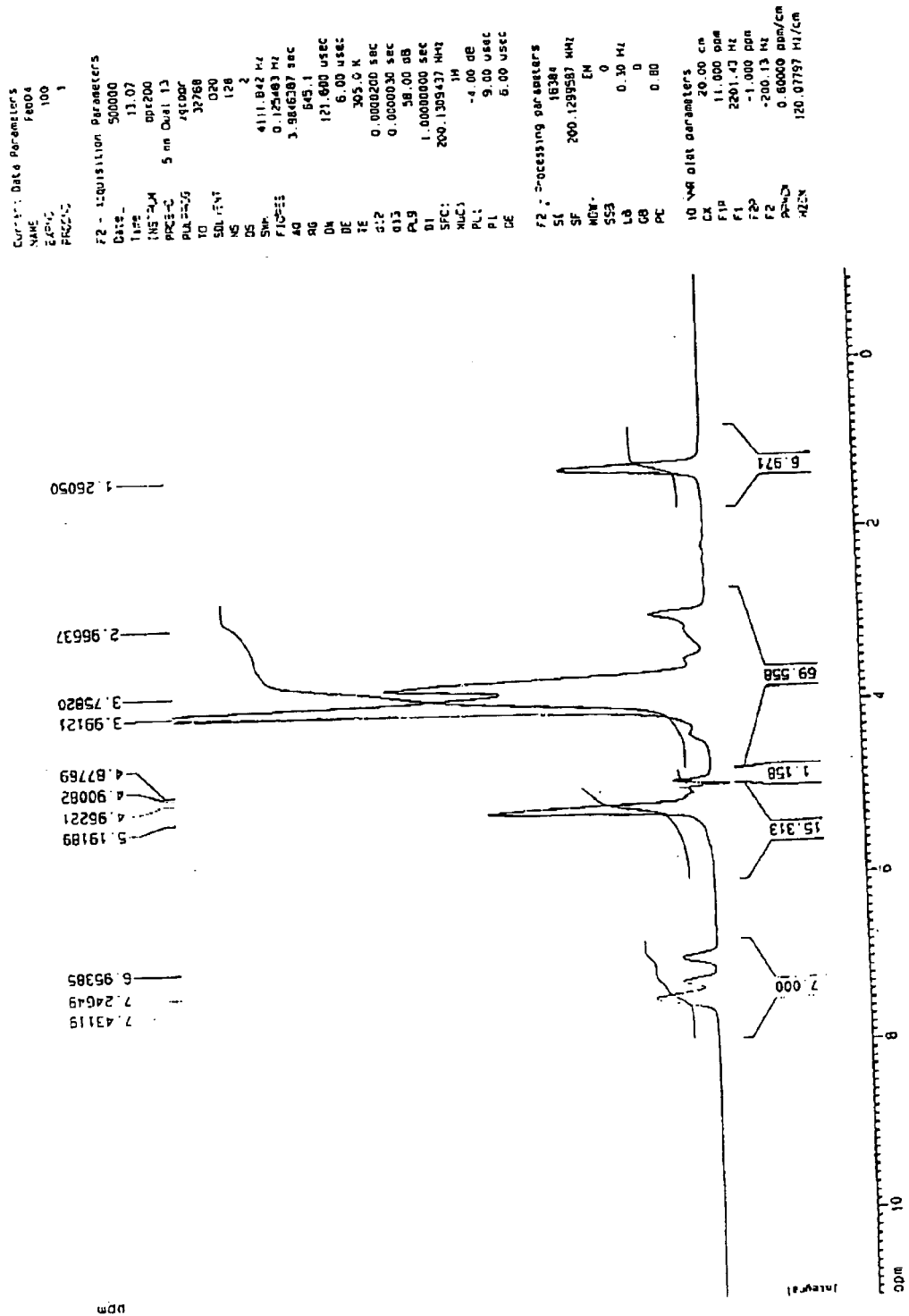
FIG. 9 shows NMR spectrum of the complex of L-Tyrosyl-D-alanyl-glycyl-N-methylphenylalanyl-glycyl-isopropylamide with beta-cyclodextrin.

FIG. 9 shows NMR spectrum of the complex of L-Tyrosyl-D-alanyl-glycyl-N-methylphenylalanyl-glycyl-isopropylamide with beta-cyclodextrin.

b) Procedure in a Solvent Mixture (Methanol/Water in the Ratio 5:20)

Beta. -cyclodextrin (1.135 g; 1.0 m mole) was dissolved in water (25 ml) at a temperature of about 70 degree C. L-Tyrosyl-D-alanyl-glycyl-N-mehylphenylalanyl-glycyl-isopropylamide (0.284 g; 0.5 m mole) in methanol (5 ml) was added and stirred for another 5 minutes. The solvents were evaporated and the complex obtained was dried in vacuum at a temperature about 40 degree C. Inclusion complex (1.36 g; 95.8%) of L-Tyrosyl-D-alanyl-glycyl-N-methylphenylalanyl-glycyl-isopropylamide with beta.-cyclodextrin was obtained in the form of a white powder in the molar ratio of 1:2.

Differential scanning calorimetry and NMR spectrum showed the same results as in the process for preparing the inclusion complex in an aqueous medium.

EXAMPLE 4

Preparation of inclusion complex of L-Tyrosyl-D-alanyl-glycyl-N-methylphenylalanyl-glycyl-isopropylamide with hydroxypropyl-beta-cyclodextrin a) Procedure in Methanolic Medium L-Tyrosyl-D-alanyl-glycyl-N-methylphenylalanyl-glycyl-isopropylamide (0 568 g; 1.0 m mole) was added to a solution of hydroxypropyl-beta-cyclodextrin (1.38 g; 1.0 m mole) in methanol (25 ml) and the obtained solution was stirred for another 5 minutes at room temperature. Methanol was then evaporated and the obtained complex was dried in vacuum at the temperature of 40 degree C. Inclusion complex (1.82 g; 93.4%) of L-Tyrosyl-D-alanyl-glycyl-N-methylphenylalanyl-glycyl-isopropylamide with hydroxypropyl-beta-cyclodextrin was obtained in the form of a white powder in the molar ratio of 1:1.

Data on reaction yields, L-Tyrosyl-D-alanyl-glycyl-N-methylphenylalanyl-glycyl-isopropylamide content in the complex (determined theoretically and experimentally-spectrophotometric determination at the wavelength of 275 nm) of the complex formed are summarised in Table 1.

Figure 10:
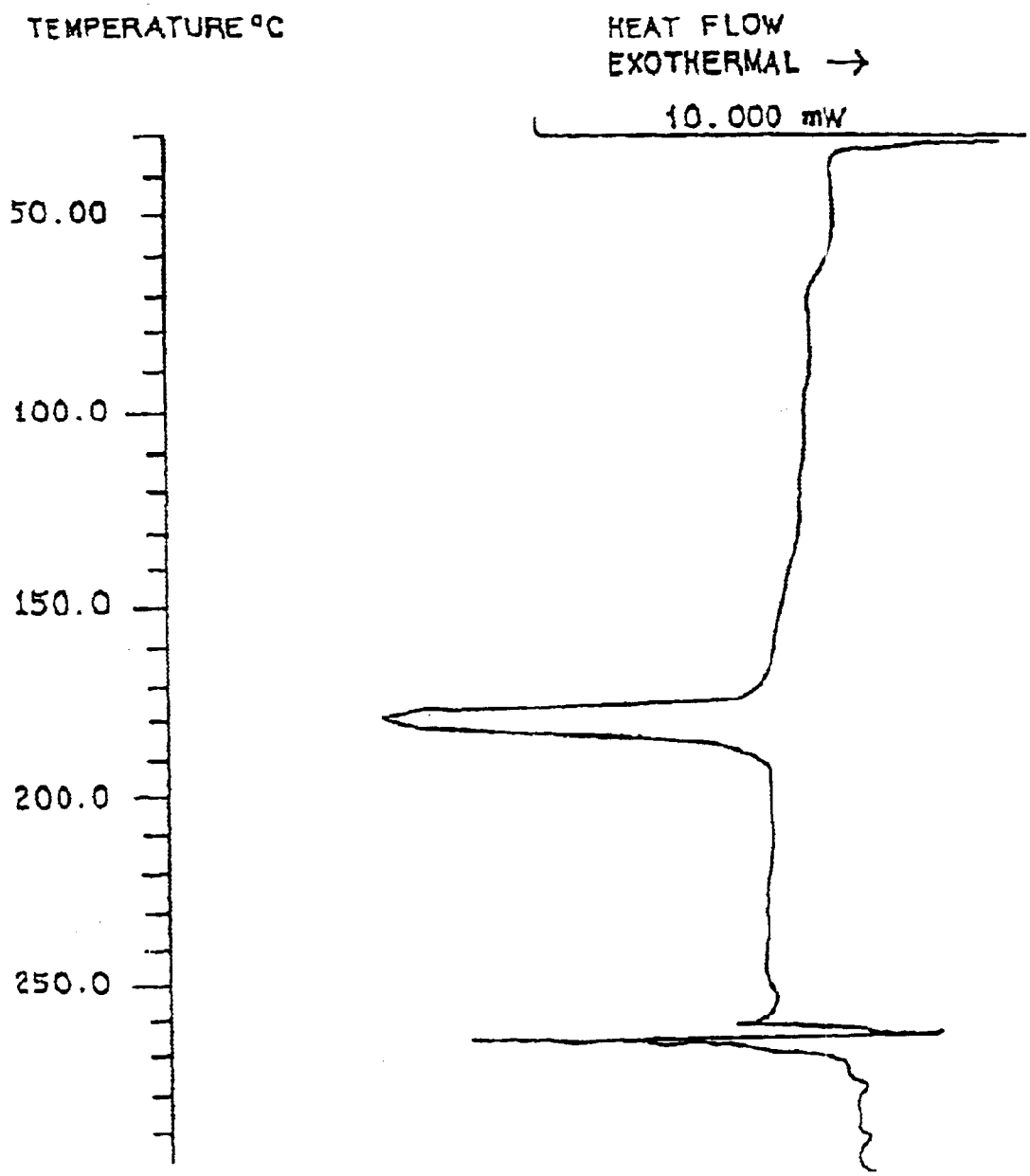
FIG. 10 shows DSC thermogram in the curve of the obtained product.

FIG. 10 shows differential scanning calorimetry (DSC thermogram)

FIG. 11 shows NMR spectrum of the complex of L-Tyrosyl-D-alanyl-glycyl-N-methylphenylalanyl-glycyl-isopropylamide with hydroxypropyl-beta-cyclodextrin.

b) Procedure in Aqueous Medium

Hydroxypropyl-beta-cyclodextrin (1.38 g; 1.0 m mole) was dissolved in water (40 ml) and the obtained solution was heated to the temperature of 70.degree C. and L-Tyrosyl-D-alanyl-glycyl-N-methylphenylalanyl-glycyl-isopropylamide (0.568 g; 1.0 m mole) was added. It was vigorously stirred for another 15 minutes and then the solution was filtered. The filtrate was frozen in liquid nitrogen and lyophilised. Inclusion complex (1.81 g, 92.9 %) of L-Tyrosyl-D-alanyl-glycyl-N-methylphenylalanyl-glycyl-isopropylamide with hydroxypropyl-beta-cyclodextrin was obtained in the form of a white powder in the molar ratio of 1.1.

Differential scanning calorimetry and NMR spectrum showed the same results as in the process for preparing inclusion complex in the methanolic medium.

EXAMPLE 5

Preparation of inclusion complex of L-Tyrosyl-D-alanyl-glycyl-N-methylphenylalanyl-glycyl-isopropylamide with hydroxyethyl-beta-cyclodextrin a) Procedure in Methanolic Medium L-Tyrosyl-D-alanyl-glycyl-N-methylphenylalanyl-glycyl-isopropylamide (0.568 g, 1.0 mmole) was added to a solution of hydroxyethyl-beta-cyclodextrin (1.44 g; 1.0 mmole) in methanol (10 ml) and the obtained solution was stirred for another 5 minutes at room temperature. Methanol was then evaporated and the obtained complex was dried in vacuo at the temperature of 40 degree C. Inclusion complex (1.87 g, 93.1 %) of L-Tyrosyl-D-alanyl-glycyl-N-methylphenylalanyl-glycyl-isopropylamide with hydroxyethyl-beta-cyclodextrin was obtained in the form of a white powder in the molar ratio of 1:1.

Differential scanning calorimetry and NMR spectrum showed the formation of inclusion complex.

b) Procedure in Aqueous Medium

Hydroxyethyl-.beta.-cyclodextrin (1.44 g; 1.0 mmole) was dissolved in water (40 ml). The obtained solution was heated to the temperature of 70.degree. C. and L-Tyrosyl-D-alanyl-glycyl-N-methylphenylalanyl-glycyl-isopropylamide (0.568 g; 1.0 mmole) was added. It was vigorously stirred for another 15 minutes and then the solution was filtered. The filtrate was frozen in liquid nitrogen and lyophilized. Inclusion complex (1.89 g; 94.1 %) of L-Tyrosyl-D-alanyl-glycyl-N-methylphenylalanyl-glycyl-isopropylamide with hydroxyethyl- beta.-cyclodextrin was obtained in the form of a white powder in the molar ratio of 1:1. Differential scanning calorimetry and NMR spectrum showed the formation of inclusion complex.

TABLE 1

Reaction yield, L-Tyrosyl-D-alanyl-glycyl-N-methylphenylalanyl-glycyl-isopropylamide content in the complex for inclusion complex of L-Tyrosyl-D-alanyl-glycyl-N-methylphenylalanyl-glycyl-isopropylamide with different derivatives of beta-cyclodextrin.

| Inclusion complex | Reaction yield (%) | % Content of L-Tyrosyl-D-alanyl-glycyl-N-methylphenylalanyl-glycyl-isopropylamide in the complex |
| --- | --- | --- |
| Beta-cyclodextrin(1:1) | 95.1 | 97.2 |
| Beta-cyclodextrin(1:2) | 93.7 | 92.88 |
| hydroxypropyl-beta-cyclodextrin(1:1) | 93.4 | 98.7 |
| hydroxyethyl-beta-cyclodextrin(1:1) | 93.1 | 97.5 |

EXAMPLE 6

30 days toxicity study or L-Tyrosyl-D-alanyl-glycyl-N-methylphenylalanyl-glycyl-isopropylamide in rat and rhesus monkey by subcutaneous route.

Compound L-Tyrosyl-D-alanyl-glycyl-N-methylphenytalanyt-glycyl-isopropylamide dissolved in saline was given daily by subcutaneous route to groups of rats (n=10 males and 10 females in each group) and rhesus monkeys (n=males and 2 females in each group) once daily for 30 consecutive days. The dose levels used in rats were 0.0, 7.5, 15.0 and 30.0 mg/kg and in monkeys 0.0, 3.75, 7.5 and 15 mg/kg. Dose levels were selected on the basis of rat ED of 3.0 mg/kg and extrapolation thereof in the monkey.

A careful general inspection of the animals was done at least once each day Cage-side observations included changes in skin and fur, eyes and mucous membranes, general activity and behavior and also general signs of abnormal functioning of respiratory, circulators, autonomic and central nervous system and somatomotor activity. Body weights (weekly in rats initial and day 30 in monkeys), daily food (rat and monkeys) and water (rat only) consumption and parameters of hematology urinalysis and blood biochemistry of the animals was recorded All the animals were sacrificed at the end of 30 days. Necropsy was performed and histopathological examination of all the important organs and tissues were done.

Urinalysis included the recording of colour, specific gravity reaction (pH) and testing for sugar, acetone, urobillinogen, bilirubin, and albumin and occult blood. Microscopic examination of urinary sediment was done for the presence of epithelial cells, WBCs, RBCs, casts, crystals and other abnormal constituents.

The hematological examinations included hemoglobin, T-RBC count mean corpuscular hemoglobin concentration, mean corpuscular volume, total leukocyte count, packed cells volume mean corpuscular volume, platelet counts, differential leukocyte counts, erythrocyte sedimentation rate (monkeys only) and prothrombin time test (monkeys only).

Biochemical estimations in blood done at day 30 in rat, and days 0 and 30 in monkeys, included glucose, creatinine, urea nitrogen, sodium, potassium SGPT (ALT), alkaline phosphatase (ALP), bilirubin, cholesterol, total serum proteins, albumin and globulin.

During necropsy examination of the external surface of the body, all orifices, and the cranial thoracic and abdominal cavities and their contents was performed. A thorough naked eye examination of size, shape, surface, colour, contours etc of all the important organs and tissues was done. Liver, kidneys, adrenals, brain, heart, lungs, spleen and gonads were weighed, and their relative weights were also calculated.

All the above mentioned organs and representative pieces from skin trachea, thyroid, different parts of the GIT pancreas, bladder, mammary glands and whole eyes were preserved in 10% buffered formalin till they were processed for paraffin embedding and sectioning.

Representative places from all the preserved organs and tissues were processed for paraffin embedding. Four to six micrometer thick sections are cut and stained by haematoxylin and eosin according to standard methods for microscopic examination.

The animals continued to remain active and healthy throughout the period of experimentation. Animals of both drug treated and control groups showed uniform (rats) or irregular (monkeys) trends of gain in body weight. The laboratory investigations showed some minor incidental variations but there was no indication of drug induced damages in the various urinalyses hematological and bloods biochemical values. Also, necropsy (including absolute and relative organ weights of important organs and histopathological examinations) did not reveal any sign of target organ toxicity.

Compound L-Tyrosyl-D-alanyl-glycyl-N-methylphenylalanyl-glycyl-isopropylamide was thus found safe in rats and rhesus monkeys in the 30-day toxicity study by subcutaneous route at the dose levels mentioned above.

EXAMPLE 7

Alleviation of Pain:

Analgesia was measured by tail flick latencies (t.f.l.) assay in rats. (D'Amour, F. E and Smith., D. L., J. Pharmacol. Exp. Ther. 72,74–79, 1941) The test required determination of tail flick latencies to heat stimulus. The basal tail flick latencies were determined twice at 10 min interval and averaged to obtain single pre drug latency. An increase in the latency by 100% or more was indicative of analgesic state of animal. A cut-off time of 10 seconds was used to avoid damage to the tail skin.

The test compounds were administered (subcutaneously or per oral) in graded dose in-groups of 8–10 rats each. Then tail flick latency was determined every 10 minutes till it was near the pre drug level. Percent of animals exhibiting analgesia was determined at each dose level of various compounds and the $ED_{50}$ along with 95% fiducial limits was calculated [Table 2] by prohibit analysis (Finney, 1971), The duration of analgesic effect was determined at the peak effect. The analgesia lasted for 5–6 hours after oral administration.

TABLE 2

| Compound/Formulation | $ED_{50}$ (mg/Kg) | |
|---|---|---|
| | S.C. route | P.O. route |
| L-Tyrosyl-D-alanyl-glycyl-N-methylphenylalanyl-glycyl-isopropylamide | 2.58 | 22.30 |
| L-Tyrosyl-D-alanyl-glycyl N-methylphenylalanyl glycyl-isopropylamide: beta CD complex (1:2) | 4.45 (equivalent to 0.89 mg of compound) | 54.23 (equivalent to 10.84 mg of compound) |

It is evident from above table that the $ED_{50}$ of beta CD complex is about one third than the compound L-Tyrosyl-D-alanyl-glycyl-N-methylphenylalanyl-glycyl-isopropylamide by subcutaneous route and was one half by oral route. The $LD_{50}$ of the compound L-Tyrosyl-D-alanyl-glycyl-N-methylphenylalanyl-glycyl-isopropylamide is 1000 mg/Kg i.p., and that of the complex is >10,000 mg/kg P. O. in mice.

EXAMPLE 8

Anti-inflammatory Action

Anti-inflammatory action was measured in vivo by the inhibition of oedema caused by carrageenin. Rats were given 250/500 mg/kg of the test substance 1 I hour before the injection of 0.1 ml 1% carrageenin suspension. The inhibition of the formed oedema was measured 3 hours after injecting carageenin. [Table 3].

TABLE 3

Measurement of anti-inflammatory action in vivo at the dosages of 500/250 mg/kg of the active substance applied per orally substance

| | Dose (p.o.) (mg/kg) | Anti-inflammatory action (210 min) |
|---|---|---|
| L-Tyrosyl-D-alanyl-glycyl-N methylphenylalanyl-glycyl-isopropyl amide:beta CD complex (1:2) | 250 | 4.0 |
| L-Tyrosyl-D-alanyl-glycyl-N-methylphenylalanyl-glycyl-isopropyl amide:beta CD complex(1:2) | 500 | 18.4 |
| L-Tyrosyl-D-alanyl-glycyl-N-methylphenylalanyl-glycyl-isopropyl amide | 50 | 19.6 |

The measurement in vivo of the anti-inflammatory action showed that the inclusion complex of L-Tyrosyl-D-alanyl-glycyl-N-methylphenylalanyl-glycyl-isopropylamide with beta cyclodextrin exhibited antiinflammatory action.

EXAMPLE 9

Effect on Gastric Mucous Membrane

Effect of L-Tyrosyl-D-alanyl-glycyl-N-methylphenylalanyl-glycyl-isopropylamide and inclusion complex of L-Tyrosyl-D-alanyl-glycyl-N-methylphenylalanyl-glycyl-isopropylamide with beta cyclodextrin on gastric mucous membrane was measured in rats. Rats were fasted overnight and were given 100 mg/kg of the active substance orally. After 4 hours its effect on irritation of gastric mucous membrane and gastric ulceration, gastric juice volume and extent of free and total acid was determined. [Table 4].

Measurement of the effect of L-Tyrosyl-D-alanyl-glycyl-N-methylphenylalanyl-glycyl-isopropylamide beta-cyclodextrin (1:1) on gastric mucous membrane

TABLE 4

| Dose (mg/kg) | Ulceration | Gastric Juice volume | Free acid | Total acid |
|---|---|---|---|---|
| 100 | — | −23 | +9.0 | +10.0 |

The above data show that L-Tyrosyl-D-alanyl-glycyl-N-methylphenylalanyl-glycyl-isopropylamide bound into an inclusion complex with beta -cyclodextrin did not exhibit an irritating effect on gastric mucous membrane of the animals

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<221> NAME/KEY: PEPTIDE
<222> LOCATION: (1)..(5)
<223> OTHER INFORMATION: Enkephalin Analogue

<400> SEQUENCE: 1

Tyr Arg Gly Phe Pro
1               5
```

EXAMPLE 10

Preparation of tablets with 125 mg of active substance [inclusion complex (1:2)] of L-Tyrosyl-D-alanyl-glycyl-N-methylphenylalanyl-glycyl-isopropylamide with beta-cyclodextrin Tablets of the Following Composition were Prepared:

TABLE 5

| Active constituent | Weight |
|---|---|
| L-Tyrosyl-D-alanyl-glycyl-N-methylphenylalanyl-glycyl isopropylamide:beta cyclodextrin complex (1:2) | 125 mg |
| lactose | 70 mg |
| methyl cellulose | 5 mg |
| magnesium stearate | 2 mg |

Preparation of tablets: The active substance was homogeneously stirred with additives. The mixture was sieved through a sieve and pressed into tablets on a rotating tableting machine and the resulting tablet properly packed in a polythene lined blister type packing to avoid coming into contact with moisture before use.

EXAMPLE 11

Preparation of transdermal tapes of active substance (inclusion complex (1:1)) of L-Tyrosyl-D-alanyl-glycyl-N-methylphenylalanyl-glycyl-isopropylamide with beta-cyclodextrin Polyvinyl alcohol (4 g) and polyvinylpyrrolidone (2 g) were taken in a beaker and stirred at 75° C., 120 ml ethyl alcohol (50%. v/v) was slowly added into this to get a fine latex. L-Tyrosyl-D-alanyl-glycyl-N-methylphenylalanyl-glycyl-isopropylamide:beta-cyclodextrin complex (1:1) (1.8) g was taken & suspended in propylene glycol (2 ml) PEG 400 (0.5 ml), poly propylene glycol (2 ml) and Triton X-100 (1.5 ml) by using sonicater Polymer latex prepared in earlier step was transferred to it by continuous stirring and further stirred for 15 minutes. The hydrogel so formed was uniformly poured into a petri dish and allowed to dry. The next day a yellow coloured patch was obtained. This was covered with the plastic film and cut into the desired size. The patches so obtained were properly packed in a polythene lined blister type packing to avoid coming into contact with moisture before use.

What is claimed is:

1. An orally efficacious and prolonged duration of action inclusion complex, consisting essentially of an opioid peptide of L-Tyrosyl-D-alanyl-glycyl-N-methylphenylalanyl-glycyl-isopropylamide and a cyclodextrin derivative, wherein said inclusion complex is formulated for oral administration to a patient in need thereof, wherein the molar ratio between said L-Tyrosyl-D-alanyl-glycyl-N-methylphenylalanyl-glycyl-isopropylamide and said cyclodextrin derivative is 1:5 to 2:1, and wherein said inclusion complex does not contain an acid component.

2. Inclusion complex as claimed in claim 1, wherein the cyclodextrin derivative is selected from beta cyclodextrin, hydroxypropyl-beta cyclodextrin, dimethyl-beta cyclodextrin, and hydroxyethyl-beta-cyclodextrin.

3. Inclusion complex as claimed in claim 1 comprising L-Tyrosyl-D-alanyl-glycyl-N-methylphenylalanyl-glycyl-isopropylamide with beta-cyclodextrin.

4. Inclusion complex as claimed in claim 1 comprising L-Tyrosyl-D-alanyl-glycyl-N-methylphenylalanyl-glycyl-isopropylamide with hydroxyethyl beta-cyclodextrin.

5. Inclusion complex as claimed in claim 1 comprising L-Tyrosyl-D-alanyl-glycyl-N-methylphenylalanyl-glycyl-isopropylamide with hydroxypropyl beta-cyclodextrin.

6. Inclusion complex as claimed in claim 1 comprising L-Tyrosyl-D-alanyl-glycyl-N-methylphenylalanyl-glycyl-isopropylamide with dimethyl beta-cyclodextrin.

7. Pharmaceutical compositions consisting essentially of a therapeutically effective amount of inclusion complex of L-Tyrosyl-D-alanyl-glycyl-N-methylphenylalanyl-glycyl-isopropylamide with the cyclodextrin derivative as claimed in claim 1 having improved analgesic activity with longer duration of action as compared with the free peptide, wherein said pharmaceutical compositions are formulated for oral administration.

8. Pharmaceutical composition as claimed in claim 7 having potential for clinical application as an analgesic.

9. A method for the treatment of acute inflammations and for alleviating pain comprising the step of oral administration of a pharmaceutical composition containing the inclusion complex as claimed in claim 1 to a patient in need thereof.

10. A method as claimed in claim 9 for the treatment of acute inflammations and for alleviating pain, which comprises an oral administration of inclusion complex of L-Tyrosyl-D-alanyl-glycyl-N-methylphenylalanyl-glycyl-isopropylamide with said cyclodextrin derivative.

11. A method for the treatment of acute inflammations and for alleviating pain, which comprises oral administration of inclusion complex of L-Tyrosyl-D-alanyl-glycyl-N-methylphenylalanyl-glycyl-isopropylamide with the cyclodextrin derivative as claimed in claim 1.

* * * * *